United States Patent
Xu et al.

(10) Patent No.: US 7,015,207 B2
(45) Date of Patent: Mar. 21, 2006

(54) USE OF N-ACETYL-D-GLUCOSAMINE IN THE MANUFACTURE OF PHARMACEUTICAL USEFUL FOR PREVENTING AND TREATING SEXUAL DISORDER

(75) Inventors: Qiwang Xu, Chongqing (CN); Junkang Liu, Chongqing (CN); Zetao Yuan, Chongqing (CN)

(73) Assignees: Third Military Medical University, Chinese People's Liberation Army, P.R. of China, Chongqing (CN); Bio-Wave Institute of Suzhou Hi-Tech New District Corporation, LTD, Jiangsu (CN)

( * ) Notice: Subject to any disclaimer, the term of this patent is extended or adjusted under 35 U.S.C. 154(b) by 0 days.

(21) Appl. No.: 10/469,325

(22) PCT Filed: Feb. 28, 2002

(86) PCT No.: PCT/CN02/00122

§ 371 (c)(1),
(2), (4) Date: Jan. 5, 2004

(87) PCT Pub. No.: WO02/067948

PCT Pub. Date: Sep. 6, 2002

(65) Prior Publication Data

US 2004/0092483 A1    May 13, 2004

(30) Foreign Application Priority Data

Feb. 28, 2001    (CN) ............... 01104883 A

(51) Int. Cl.
*A01N 43/04*    (2006.01)
*A61K 31/70*    (2006.01)
(52) U.S. Cl. .......................... 514/62; 514/23
(58) Field of Classification Search ............... 514/62
See application file for complete search history.

(56) References Cited

U.S. PATENT DOCUMENTS 4,772,591 A * 9/1988 Meisner .................. 514/62

FOREIGN PATENT DOCUMENTS

| CN | 1156026 | 8/1997 |
| CN | 1156027 | 8/1997 |
| CN | 1156028 | 8/1997 |
| WO | 93/14765 | 8/1993 |
| WO | 93/18775 | 9/1993 |

* cited by examiner

*Primary Examiner*—James O. Wilson
*Assistant Examiner*—Traviss C. McIntosh, III
(74) *Attorney, Agent, or Firm*—Ladas & Parry

(57) ABSTRACT

The present invention has disclosed a use of N-acetyl-D-glucosamine in the preparation of a medicine for preventing and treating the sexual disfunction. The preparation taken N-acetyl-D-glucosamine as a main active component has been used to prevent and cure the sexual disfunction, and has the merits of remarkable curative effect, easy to prepare, no side effect and so on.

11 Claims, No Drawings

USE OF N-ACETYL-D-GLUCOSAMINE IN THE MANUFACTURE OF PHARMACEUTICAL USEFUL FOR PREVENTING AND TREATING SEXUAL DISORDER

TECHNICAL FIELD

The present invention relates to the use of N-acetyl-D-glucosamine and pharmaceutical acceptable salts thereof in the manufacture of a medicament for preventing and treating the sexual disfunction.

BACKGROUND ART

At present, there are many kinds of medicines for preventing and treating the sexual disfunction in China and other countries, which are mainly divided into two big categories: (1) the medicines with viagra as a representative one, which acts on the endothelium cell of blood vessel for regulating and improving the blood flux in the sexual organs and improving the sexual disfunction one-pass in a short period. But this medicine has a shortcoming of having a large side effect of substantially influencing cardiac function; (2) Chinese traditional medicines, which are able to benefit liver and kidney by systematic regulation and has a certain effect, but their starting-effect is too slow. So it is necessary to develop a new medicine for preventing and treating the sexual disfunction.

In the research of "bio-waves" theory, the present inventor has set up a bacterial wave growth model. Through researching, it is known that this wave is of its intrinsic regulation mechanism: some chemical substances are able to participate the regulation in the bio-wave process, so as to transform an abnormal periodic slow wave into a normal physiological chaotic quick wave, and this kind of substances are known as promoting wave factors. Through separating, purifying and identifying, it is determined that one of the factors is N-acetyl-D-glucosamine, the promoting wave function of which is shown in regulating the coupling oscillation of cellular membrane protein and sugar coating. Many biochemical and physiological process of human body need the participation of the promoting wave factors, and it would lead to an abnormal state, if this kind of promoting wave factors is lacked in the living body.

N-acetyl-D-glucosamine is a chemical reagent. From the 1990's, it is continually used to treat pericementitis (WO9102530A1), microbiological infection (WO9718790A3), intestinal inflammation (WO9953929A1), cornea disease (JP10287570A2), hypertrophy of the prostate (US05116615) and so on. It is also applied in cosmetology (JP59013708A2), shampoo preparation (JP2011505A2), tissue growth regulation agent (WO/A 8 702244), and etc., but it has not been used in the manufacture of a medicament for preventing and treating sexual disfunction.

The applicant of the present invention is surprised to find that N-acetyl-D-glucosamine and pharmaceutical acceptable salts thereof are able to prevent and cure sexual disfunction quickly and efficiently, and said compounds almost have no toxicity. Therefore, this agent can overcome the shortcomings existed in the current medicaments for preventing and treating sexual function as mentioned above.

CONTENTS OF THE INVENTION

Therefore, the present invention is related to the use of N-acetyl-D-glucosamine and pharmaceutical acceptable salt thereof in the manufacture of a medicament for preventing and treating sexual disfunction.

On the other hand, the present invention is related to a method for preventing and treating sexual disfunction, including administrating to a patient who is in need thereof an effective amount of N-acetyl-D-glucosamine and pharmaceutical acceptable salts thereof to prevent and cure the sexual disfunction.

The molecular formula of N-acetyl-D-glucosamine is $C_8H_{15}NO_6$, its structure is as follows:

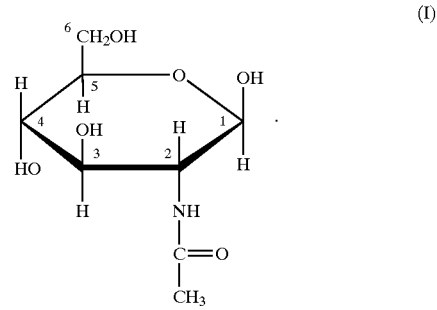

(I)

N-acetyl-D-glucosamine can be purchased in market or prepared according to a known method. For instance, patent application WO97/31121 has disclosed a method for preparing N-acetyl-D-glucosamine from chitin by enzyme method, Japanese patent application JP63273493 has disclosed a method in which chitin is partially hydrolyzed into N-acetyl-chitose, and then it is treated with enzyme to obtain N-acetyl-D-glucosamine.

The pharmaceutical acceptable salts of N-acetyl-D-glucosamine that can be mentioned are the salts formed with pharmaceutical acceptable acids, for instance, the salts formed with inorganic acids, such as hydrochloride, hydrobromide, borate, phosphate, sulfate sulfite and hydrophosphate, and the salts formed with organic acids, such as citrate, benzoate, ascorbate, methyl sulfate, naphthalene-2-sulfonate, picrate, fumarate, maleate, malonate, oxalate, succinate, acetate, tartrate, mesylate, tosylate, isethionate, α-ketoglutarate, α-glyceryl phosphate and glucose-1-phosphate.

Generally, the compound of the present invention is administrated by oral, parenteral, sublingual, or penetrating skin, preferably, administrated by oral. In the course of treating sexual disfunction according to the present invention, the amount of active component to be taken is dependent upon the features and seriousness of the disease and the weight of the patient body. The preferred dosage unit usually comprises 5~1000 mg, favorably 10~700 mg, preferably 20~500 mg product. Preferably, the concentration of the active component in the medical preparation is 0.1~10% (by weight). These unit dosages are generally administrated once or more times daily and the total dosage for a person to be taken daily is varied in the range from 10 to 1000 mg, preferably 50~5000 mg/day, for instance, 100~1000 mg/day, more often 100~500 mg/day.

The pharmaceutical composition of the invention for treating the indication mentioned above are suitable for administration by oral, sublingual, subcutaneous, intramuscle, intravein, penetrating skin, or rectum, the active component is able to be applied to animal and human being in the form of dosage unit, such as in the form of freeze drying product or be mixed form with conventional pharmaceutical carrier. A suitable unit form of administration includes oral form, such as orally dispersible tablet, capsule, powder, granule and solution or suspension; the form for administrating via sublingle or buccal; the form for administrating via subcutaneous, intramuscle or intravein; the form for local or rectum administration. The prepared preparation for oral administration is particularly aqueous solution, alcoholic solution and capsule.

Solid composition in the form of tablet are made by mixing the main active component with pharmaceutial excipient, such as gelatin, starch, lactose, magnesium stearate, talc powder, Arabic gum and etc., The tablet is able to be coated with sugar or other suitable substances, or making them possess a persistent and delayed function and continually release pre-determined amount of active component.

The preparation in from of capsule can be obtained by mixing active component with diluent, and filling the obtained mixture into soft or hard capsule.

The preparation in the form of syrup or elixer may comprise active component and sweetener that would better have no caloric, methyl p-hydroxybenzoate and propyl p-hydroxybenzoate as antiseptic agent, and fragrancing agent and suitable coloring material.

The water-dispersible powder and granular preparation may comprise active component, mixed with dispersing agent or wetting agent, or suspending agent, such as polyvinylpyrrolidone, and sweetener or taste regulating agent.

The suppository for rectum administration is prepared with an adhesive which is melted at the same temperature as that of rectum, such as cocoa oil or polyethylene glycol.

The injectable aseptic aqueous solution, salt solution, alcoholic solution or homogenous suspension of the compound of the present invention can be administrated parenterally.

The applicant of the present invention believes that, through regulating bio-waves, promoting redistribution of cell and coupling oscillation between sugar coatings of cell membrane acceptor and protein, raising the sensitiveness of the local sexual hormone acceptor of sexual organ can quickly and effectively prevent and cure the sexual disfunction and have a stable curative effect in a long period.

Optimal Mode for Carrying Out the Invention

The following experimental examples are used to illustrate the promoting wave function, low toxicity and effectiveness for preventing and treating the sexual disfunction of the compound of the present invention (the compound of formula (I)).

I. Promoting wave test of the compound of formula (I)
 1. Experimental materials and method:
 1.1 Samples: pure compound of formula (I)
 1.2 Experimental materials:
 Strain: Proteus Mirabilis (which should comply with the following biological reaction characteristics: dynamics (+), urease (+), lactose (−), glucose (+), $H_2S$ (−), phenylalanine deaminase (+).
 Culture medium: modified LB culture medium (the component of the composition are: trytones of 1%, yeast extract of 0.5%, sodium chloride 1%, glucose of 0.1%, TTC of 0.002% and pH=7.2~7.4).
 1.3 Experimental method:
 The Proteus Mirabilis were inoculated at the center of LB plate, incubating at 37° C. for 9 hours, then there were concentric rings emerged, which were extended outward continually with an interval of 3 hours, and this was taken as a control; adding the compound of formula (I) with final concentration of 0.5% onto the LB plate, The Proteus Mirabilis were innoculated by the same method, cultured at 37° C., and the result showed that not only the concentric rings formed with an interval of 3 hours were emerged, comparing with the control, it can be seen that there were also many fine waves on each ring emerged.

2. Experimental results and evaluation:
 The experiment adopts a bio-wave model which is used to research the promoting wave function of the compound of formula (I). It can be seen from the result that the compound of formula (I) was not only able to cause bacterial cell to reveal a normal bio-wave characteristic, but also cause the wave reveal finer wave mode so as to make the wave period to be shorten, and these indicated that the compound of formula (I) have promoting function to bio-waves, and the promoting wave function is able to participate regulation of the re-distribution function of the cells in the body and the two-step effect of conducting sexual excitation led by sexual hormone acceptor on the membrane surface, so that this is a basis of the function for preventing and treating the sexual disfunction of the compound of formula (I).

II. Toxicological test of the compound of formula (I), including:
 1. acute toxicity test: including tests of administrating medicine by oral, intravenous injection and maximum limit amount for administration;
 2. Ames test;
 3. micronucleus test of bone marrow cell of small mouse;
 4. abnormal sexual test for the sperm of mouse;
 5. abnormal aberrance test for the chromosin of mouse's testis;
 6. chronic lethal test;
 7. subchronic toxicity (feed for 90 days) test;
 8. traditional deformity-inducing test;

The results from these tests show that in the acute toxicity test of the compound of formula (I), the dosage more than 2 g/kg is taken, which is 300 times than the injection dosage for human being, but the acute toxicosis reaction had not appeared yet; in the long-period toxicity test, the maximum dosage has reached up to 1 g/kg, and after the treatment and observation for four weeks, there is no intoxication reaction yet; and in the reproduction test, the mouse was feed from routine dosage of 7 mg/kg for 3 generations, it has been proved that the compound of formula (I) has no influence on the pregnancy, birth, nurse and the growth of baby mouse, so it is proved that the compound of formula (I) is a substance without toxicity.

III. Clinic tests 32 examples of male patients were picked out, who had been repeatedly treated for sexual disfunction with current treatment method, but these treatments were failed, the patients are classified clinically into heavy, medium and light degree disease, separately administrated with N-acetyl-D-glucosamine in the form of capsule by oral (500 mg/day) and alcoholic solution (50 mg/1000 ml) by oral (10 ml/day), using two weeks as a period of treatment, and before and after the administration, and comparing the condition of the patient's symptom by detecting luteinizing hormone (LH), follicular stimulating hormone (FSH), prolactin (PRL), testosterone (T), estradiol (E2) and local blood flux. The results showed that, after treatment, 23 patients became normal, other 7 patient had been turned from heavy and medium degree into light degree of the clinic classification, 2 patients were failed (one of them was more than 70 years old, and the another one was suffered from prostate swelling, which influenced on the curative effect). The cure rate is 72%, the total effective rate is 90% (showed by certifications of clinic treating effects). The time for administration coming into effect was from 1 hour after first administrating medicine to one week after continually administrating the medicine, so it is different in time. After treatment, the curative effect was steady and could be maintained for a long time. In another test for volunteers, a voluntary patient suffered from disfunction for more than ten years had taken by oral 12 grains of capsules (500 mg/grain) of the compound of formula (I) in three days, then his sexual function was recovered to normal, and keep normal over two years up to now.

The invention claimed is:

1. A method of treating sexual dysfunction in a male subject, wherein the sexual dysfunction is characterized by an abnormal level of a sexual hormone that results from a decreased sensitivity of a sexual hormone acceptor in said subject, the method comprising administering to the subject a medicament comprising N-acetyl-D-glucosamine and/or a pharmaceutically acceptable salt thereof in an amount to normalize the level of the hormone in the subject.

2. The method according to claim 1, wherein said medicament is administrated to the subject orally.

3. The method according to claim 2, wherein said medicament is in the form of aqueous solution, alcoholic solution or capsule.

4. The method according to any one of claims 1 to 3, wherein the daily dosage for administration is in the range of 10~1000 mg of N-acetyl-D-glucosamine and/or pharmaceutically acceptable salts thereof for each subject.

5. The method according to claim 2, wherein the daily dosage administration is in the range of 10~1000 mg of N-acetyl-D-glucosamine and/or pharmaceutically acceptable salts thereof for each subject.

6. The method according to claim 3, wherein the daily dosage for administration is in the range of 10~1000 mg of N-acetyl-D-glucosamine and/or pharmaceutically acceptable salts thereof for each subject.

7. The method according to claim 1, wherein the hormone is selected from the group consisting of luteinizing hormone, follicular stimulating hormone, prolactin, testosterone, and estradiol.

8. A method of treating sexual dysfunction in a subject, wherein the sexual dysfunction is characterized by an abnormal level of a hormone selected from the group consisting of luteinizing hormone, follicular stimulation hormone, prolactin, testosterone, and estradiol, the method comprising the step of administering to said subject a medicament comprising N-acetyl-D-glucosamine and/or a pharmaceutically acceptable salt thereof, said medicament being administered to said subject in an amount effective to normalize the hormone in said subject.

9. The method according to claim 8, comprising the step of determining the level of the hormone in the subject prior to said administering step.

10. The method according to claim 9, comprising the step of determining the level of the hormone in the subject after the administering step.

11. The method according to claim 8, wherein the subject is a male.

* * * * *